(12) United States Patent
Vreeman

(10) Patent No.: US 8,617,103 B2
(45) Date of Patent: Dec. 31, 2013

(54) ANGLED TIP CATHETER

(75) Inventor: Daniel J. Vreeman, Elk River, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/314,441

(22) Filed: Dec. 8, 2011

(65) Prior Publication Data
US 2012/0078175 A1    Mar. 29, 2012

Related U.S. Application Data

(63) Continuation of application No. 12/355,327, filed on Jan. 16, 2009, now abandoned.

(60) Provisional application No. 61/021,947, filed on Jan. 18, 2008.

(51) Int. Cl.
*A61M 29/00*    (2006.01)

(52) U.S. Cl.
USPC ..................................... 604/96.01

(58) Field of Classification Search
USPC ............................ 604/95.04, 96.01, 523, 525
See application file for complete search history.

(56) References Cited

U.S. PATENT DOCUMENTS

| | | |
|---|---|---|
| 4,617,019 A | 10/1986 | Fecht et al. |
| 4,850,960 A | 7/1989 | Grayzel |
| 5,037,403 A | 8/1991 | Garcia |
| 5,300,048 A | 4/1994 | Drewes, Jr. et al. |
| 5,425,903 A | 6/1995 | Sloane, Jr. et al. |
| 5,443,457 A | 8/1995 | Ginn et al. |
| 5,736,085 A | 4/1998 | Brown et al. |
| 5,797,961 A * | 8/1998 | Smith et al. ............ 606/222 |
| 5,827,229 A | 10/1998 | Auth et al. |
| 5,843,356 A | 12/1998 | Patel et al. |
| 5,873,864 A | 2/1999 | Luther et al. |
| 5,985,195 A | 11/1999 | Muskatello |
| 6,659,950 B2 | 12/2003 | Taheri |
| 6,767,338 B2 | 7/2004 | Hawk et al. |
| 6,855,124 B1 | 2/2005 | Gonzalez et al. |
| 7,250,042 B2 | 7/2007 | Kataishi et al. |
| 2003/0060784 A1 * | 3/2003 | Hilgers et al. ............ 604/272 |
| 2004/0158136 A1 * | 8/2004 | Gough et al. ............ 600/328 |

(Continued)

FOREIGN PATENT DOCUMENTS

| | | |
|---|---|---|
| EP | 0 652 024 B1 | 5/1995 |
| WO | WO 99/25412 A2 | 5/1999 |
| WO | WO 2006/124702 A2 | 11/2006 |
| WO | WO 2007/067324 A1 | 6/2007 |

OTHER PUBLICATIONS

Mar. 19, 2009 Invitation to Pay Additional Fees and, Where Applicable, Protest Fee in PCT Application No. PCT/US2009/031270 (8 pages).

(Continued)

*Primary Examiner* — Aarti B Berdichevsky
(74) *Attorney, Agent, or Firm* — Alana T. Bergman, Esq.

(57) ABSTRACT

A catheter having improved ability to cross body passage obstructions and that more easily allows backloading of a guidewire into the lumen of the catheter is comprised of a tip, a shaft, and a lumen. The distal end of the catheter tip is oriented at an angle other than 90° to the lengthwise axis of the catheter tip. A guidewire may be easily backloaded into the elongated catheter lumen at the location of the angled catheter tip.

31 Claims, 4 Drawing Sheets

(56) References Cited

U.S. PATENT DOCUMENTS

2005/0080399 A1    4/2005  Bolmsjo et al.
2006/0100572 A1    5/2006  DiMatteo et al.
2007/0167822 A1    7/2007  Webler et al.
2010/0106104 A1*   4/2010  Villette ........................ 604/272
2011/0208114 A1*   8/2011  Morlet ........................... 604/22

OTHER PUBLICATIONS

Jun. 22, 2009 International Search Report and Written Opinion of PCT Application No. PCT/US2009/031270 (23 pages).

* cited by examiner

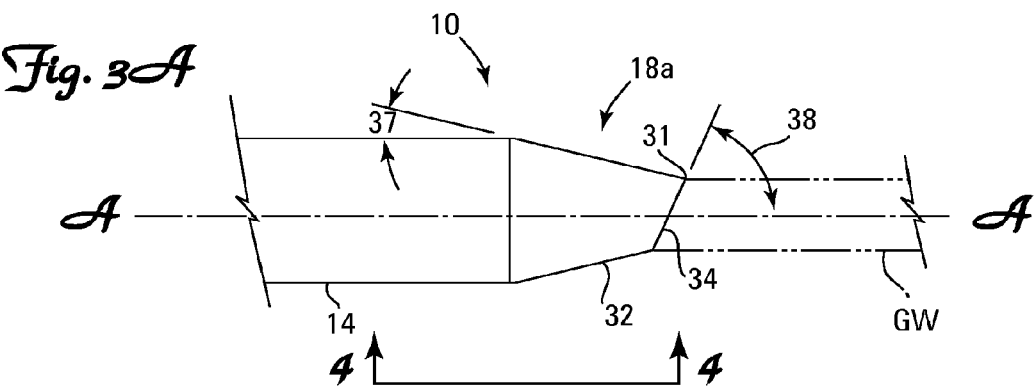
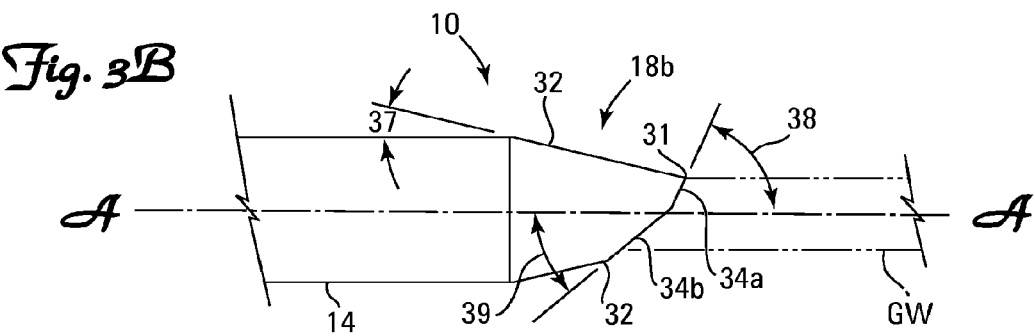
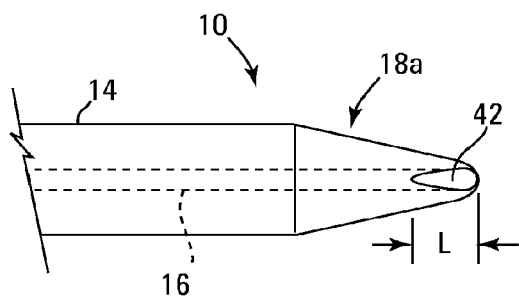

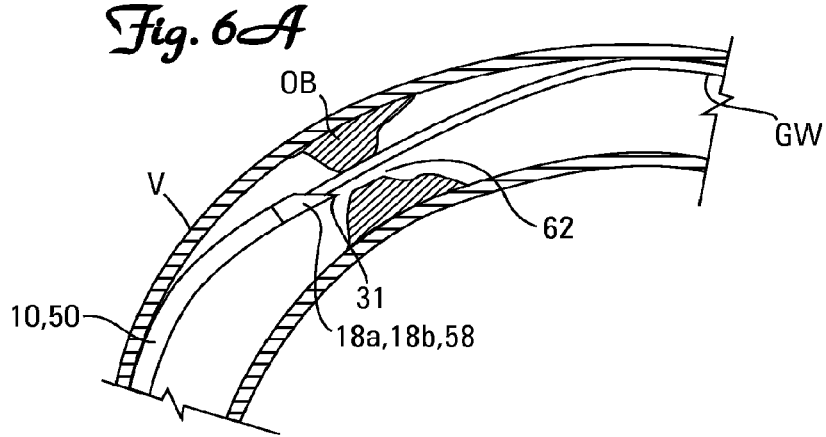
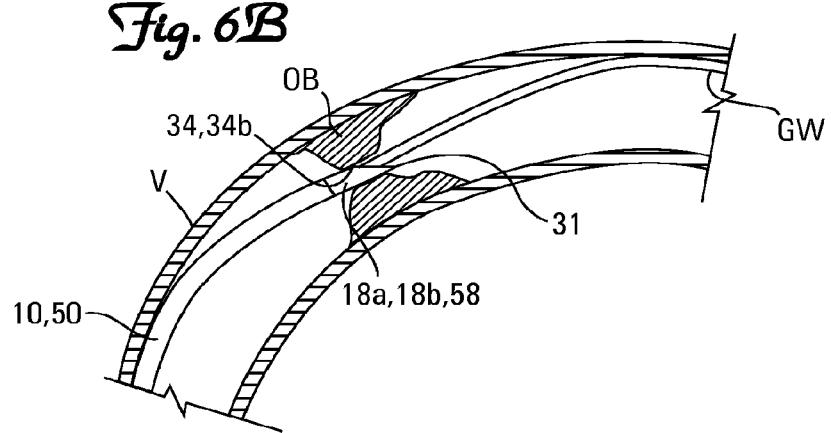
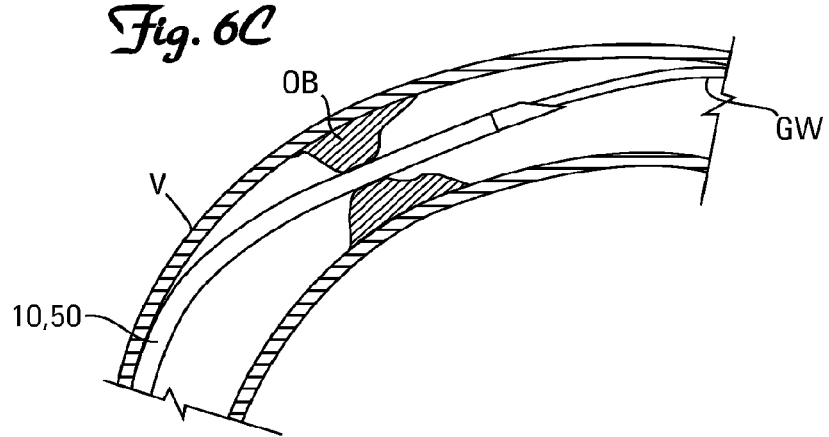

ANGLED TIP CATHETER

This application is a continuation of application Ser. No. 12/355,327, filed Jan. 16, 2009, which claims the benefit of U.S. Provisional Application No. 61/021,947, filed Jan. 18, 2008, entitled "Angled Tip Catheter", the contents of each of which are hereby incorporated by reference herein.

FIELD OF THE INVENTION

The present invention relates to catheters for advancement to a site in a body. More particularly, this invention pertains to a catheter for advancement across an obstruction in a body passage.

BACKGROUND OF THE INVENTION

Catheters are commonly used for advancement into a body passage for purposes such as diagnosis or treatment of medical conditions. Examples of such passages include but are not limited to a carotid artery, coronary artery, femoral artery, other blood vessel, a ureter, urethra, bronchus, esophagus, or other passage. Examples of such catheters include but are not limited to diagnostic, guide, balloon (PTCA, PTNA or PTA), stent delivery (BES, SES or DES), drug delivery, infusion, aspiration, atherectomy, thrombectomy, embolic protection device delivery, embolic protection device recovery, and others. Such catheters are typically used by first advancing a guidewire into the body passage, backloading the proximal end of the guidewire into the distal end of a catheter lumen, and advancing the catheter over the guidewire to a region of interest.

It is not unusual for the body passage to be partially obstructed due to atherosclerotic disease, tumors, mechanical causes (May-Thurners syndrome), or other causes. Advancing catheters past the obstruction can be difficult and time consuming. Part of the problem is that in conventional catheters there is generally not a smooth transition from the guidewire outer diameter to the catheter outer diameter. The mismatch between said diameters becomes an impediment to successful catheter advancement across an obstruction.

There are some catheters in the market addressing the problem of advancement past an obstruction but they are generally expensive and their results are operator dependent. For example, steerable catheters have been tried, as well as laser catheters and blunt dissectors. Both of these latter approaches carry a risk of perforation of the passage wall, and ablative technologies generate potentially harmful ablated materials.

Another problem encountered with these catheters is that the backloading of guidewires into catheter lumens can be difficult due to dim lighting in most catheterization labs and farsightedness of older practitioners. There have been some accessory devices marketed to simplify the process of backloading guidewires into catheter lumens but none have seen widespread adoption in the market.

What is needed is a catheter having improved ability to cross body passage obstructions and a catheter that more easily allows backloading of a guidewire into the lumen of the catheter.

SUMMARY OF THE INVENTION

The invention provides a catheter having improved ability to cross body passage obstructions and that more easily allows backloading of a guidewire into the lumen of the catheter is comprised of a tip, a shaft, and a lumen. The distal end of the catheter tip is oriented at an angle other than 90° to the lengthwise axis of the catheter tip. A guidewire may be easily backloaded into the elongated catheter lumen at the location of the angled catheter tip. The catheter shaft has characteristics that facilitate orienting the tip angle relative to a body passage obstruction.

The invention provides a catheter comprising an elongate shaft, a distal tip, and a lumen extending proximally from the distal tip, a first distal end of the distal tip being oriented at a first angle other than 90 degrees to the lengthwise axis of the catheter tip, a second distal end of the distal tip being oriented at a second angle other than 90 degrees to the lengthwise axis of the catheter tip, the second distal end of the distal tip being adjacent to the first distal end of the distal tip, the second distal end of the distal tip being proximal of the first distal end of the distal tip, and the second angle being less than the first angle.

The invention provides a catheter comprising an elongate shaft having a length, a distal tip, and a lumen extending proximally from the distal tip, a distal end of the distal tip being oriented at an angle other than 90 degrees to the lengthwise axis of the catheter tip, and the shaft having a length and the shaft having a bend at least from the distal tip to a point 10 percent of the shaft length proximal from the distal tip.

The invention provides a catheter comprising an elongate shaft, a distal tip, and a lumen extending proximally from the distal tip, a distal end of the distal tip being oriented at an angle other than 90 degrees to the lengthwise axis of the catheter tip, the distal tip comprising a tapered region, and the catheter being a balloon catheter.

The invention provides an assembly comprising a guidewire and a catheter described herein. The invention provides a method of advancing a catheter into a body lumen of a patient comprising: loading a guidewire into the lumen of a catheter of described herein; advancing the guidewire into the body lumen; and advancing the catheter over the guidewire into the body lumen.

It is to be understood that that both the foregoing general description and the following detailed description are exemplary and explanatory and are intended to provide further explanation of the invention as claimed.

BRIEF DESCRIPTION OF THE DRAWINGS

The above and further advantages of the invention may be better understood by referring to the following description in conjunction with the accompanying drawings.

FIGS. 3A and 3B illustrate side elevation views of embodiments of catheter tips having features in accordance with the principles of the present disclosure, with a conventional guidewire shown in phantom line.

FIG. 4 illustrates a plan view of the catheter tip illustrated in FIG. 3A having features in accordance with the principles of the present disclosure.

FIGS. 6A, 6B, and 6C illustrate use of a catheter and conventional guidewire in a body passage in accordance with the principles of the present disclosure.

DETAILED DESCRIPTION

Figure 1:
FIG. 1 illustrates a side elevation view of an embodiment of a catheter having features in accordance with the principles of the present disclosure.

The invention provides a catheter comprising an elongate shaft, a distal tip, and a lumen extending proximally from the distal tip, a first distal end of the distal tip being oriented at a first angle other than 90 degrees to the lengthwise axis of the catheter tip, a second distal end of the distal tip being oriented at a second angle other than 90 degrees to the lengthwise axis of the catheter tip, the second distal end of the distal tip being adjacent to the first distal end of the distal tip, the second distal end of the distal tip being proximal of the first distal end of the distal tip, and the second angle being less than the first angle. In an embodiment, the first angle is from 70 degrees to 20 degrees. In another embodiment, the first angle is selected from the group consisting of 65, 60, 55, 50, 45, 40, 35, or 30 degrees. In an embodiment, the second angle is from 60 to 10 degrees. In another embodiment, the second angle is selected from the group consisting of 55, 50, 45, 40, 35, 30, 25, or 20 degrees. In an embodiment, the first angle is 65 degrees and the second angle is 55 degrees. In another embodiment, the second angle is to 20 degrees less than the first angle. In an embodiment, the second angle is 10 degrees less than the first angle.

In an embodiment, the shaft has a length of 10 cm to 300 cm. In another embodiment, the shaft has a length of 20 cm. In an embodiment, the distal tip comprises a tapered region. In another embodiment, the tapered region has an angle relative to the lengthwise axis of the catheter tip of 1 to 16 degrees. In an embodiment, the distal tip has a length of 2 mm to 12 mm. In an embodiment, the lumen extends proximally from the distal end of the distal tip. In another embodiment, the lumen extends proximally from the distal end of the distal tip to a proximal end of the shaft.

In an embodiment, the shaft has a length and the shaft has a bend over at least some of its length. In another embodiment, the shaft has a bend over all of its length. In an embodiment, the shaft has a bend at least from the distal tip to a midpoint of the shaft. In another embodiment, the shaft has a bend at least from the distal tip to a point 25 percent of the shaft length proximal from the distal tip. In an embodiment, the shaft has a bend at least from the distal tip to a point 10 percent of the shaft length proximal from the distal tip. In an embodiment, the shaft has a maximum concavity of from 0.2 cm to 2 cm as measured over a length of 10 cm. In another embodiment, the shaft has a maximum concavity selected from the group consisting of 0.4 cm, 0.6 cm, 0.8 cm, 1.0 cm, 1.2 cm, 1.4 cm, 1.6 cm, and 1.8 cm. In an embodiment, the shaft has a maximum concavity of 0.4 cm. In an embodiment, the catheter is a balloon catheter.

The invention provides a catheter comprising an elongate shaft having a length, a distal tip, and a lumen extending proximally from the distal tip, a distal end of the distal tip being oriented at an angle other than 90 degrees to the lengthwise axis of the catheter tip, and the shaft having a length and the shaft having a bend at least from the distal tip to a point 10 percent of the shaft length proximal from the distal tip. In an embodiment, the shaft has a bend over all of its length. In another embodiment, the shaft has a bend at least from the distal tip to a midpoint of the shaft. In an embodiment, the shaft has a bend at least from the distal tip to a point 25 percent of the shaft length proximal from the distal tip. In an embodiment, the shaft has a maximum concavity of from 0.2 cm to 2 cm as measured over a length of 10 cm. In another embodiment, the shaft has a maximum concavity selected from the group consisting of 0.4 cm, 0.6 cm, 0.8 cm, 1.0 cm, 1.2 cm, 1.4 cm, 1.6 cm, and 1.8 cm. In an embodiment, the shaft has a maximum concavity of 0.4 cm.

In an embodiment, the angle is from 70 degrees to 20 degrees. In another embodiment, the angle is selected from the group consisting of 65, 60, 55, 50, 45, 40, 35, and 30 degrees. In an embodiment, the shaft has a length of 10 cm to 300 cm. In an embodiment, the shaft has a length of 20 cm. In an embodiment, the distal tip comprises a tapered region. In another embodiment, the tapered region has an angle relative to the lengthwise axis of the catheter tip of 1 to 16 degrees. In an embodiment, the distal tip has a length of 2 mm to 12 mm. In an embodiment, the lumen extends proximally from the distal end of the distal tip. In another embodiment, the lumen extends proximally from the distal end of the distal tip to a proximal end of the shaft. In an embodiment, the catheter is a balloon catheter.

The invention provides a catheter comprising an elongate shaft, a distal tip, and a lumen extending proximally from the distal tip, a distal end of the distal tip being oriented at an angle other than 90 degrees to the lengthwise axis of the catheter tip, the distal tip comprising a tapered region, and the catheter being a balloon catheter. In an embodiment, the angle is from 70 degrees to 20 degrees. In another embodiment, the angle is selected from the group consisting of 65, 60, 55, 50, 45, 40, 35, and 30 degrees. In an embodiment, the shaft has a length of 10 cm to 300 cm. In another embodiment, the shaft has a length of 20 cm. In an embodiment, the tapered region has an angle relative to the lengthwise axis of the catheter tip of 1 to 16 degrees. In an embodiment, the distal tip has a length of 2 mm to 12 mm. In an embodiment, the lumen extends proximally from the distal end of the distal tip. In another embodiment, the lumen extends proximally from the distal end of the distal tip to a proximal end of the shaft.

The invention provides an assembly comprising a guidewire and a catheter described herein.

The invention provides a method of advancing a catheter into a body lumen of a patient comprising: providing a catheter, the catheter comprising an elongate shaft, a distal tip, and a lumen extending proximally from the distal tip, a first distal end of the distal tip being oriented at a first angle other than 90 degrees to the lengthwise axis of the catheter tip, a second distal end of the distal tip being oriented at a second angle other than 90 degrees to the lengthwise axis of the catheter tip, the second distal end of the distal tip being adjacent to the first distal end of the distal tip, the second distal end of the distal tip being proximal of the first distal end of the distal tip, and the second angle being less than the first angle; loading a guidewire into the lumen of the catheter; advancing the guidewire into the body lumen; and advancing the catheter over the guidewire into the body lumen. In an embodiment, the catheter traverses an obstruction in the body lumen. In another embodiment, the body lumen is a blood vessel. In an embodiment, the shaft has a length, the shaft has a bend over at least some of its length, and the shaft has a maximum concavity of 0.2 cm to 2 cm as measured over a length of 10 cm, and wherein the catheter self-orients on the guidewire such that the maximum concavity is aligned with a maximum convex curvature of the guidewire. In another embodiment, the guidewire is advanced into the body lumen such that it traverses an obstruction in the body lumen, the guidewire having a bend at a portion of the guidewire that traverses the obstruction, the bend creating a gap between the guidewire and the obstruction, the method further comprising orienting a distal most portion of the distal tip so that the distal most portion of the distal tip traverses the obstruction through the gap as the catheter traverses the obstruction. In an embodiment, the orienting of the distal most portion of the distal tip occurs because the catheter self-orients on the guidewire. In an embodiment, the catheter is a balloon catheter.

The invention provides a method of advancing a catheter into a body lumen of a patient comprising: providing a catheter, the catheter comprising an elongate shaft having a length, a distal tip, and a lumen extending proximally from the distal tip, a distal end of the distal tip being oriented at an angle other than 90 degrees to the lengthwise axis of the catheter tip, and the shaft having a length and the shaft having a bend at least from the distal tip to a point 10 percent of the shaft length proximal from the distal tip; loading a guidewire into the lumen of the catheter; advancing the guidewire into the body lumen; and advancing the catheter over the guidewire into the body lumen. In an embodiment, the catheter traverses an obstruction in the body lumen. In another embodiment, the body lumen is a blood vessel. In an embodiment, the shaft has a maximum concavity of 0.2 cm to 2 cm as measured over a length of 10 cm, and wherein the catheter self-orients on the guidewire such that the maximum concavity is aligned with a maximum convex curvature of the guidewire. In an embodiment, the guidewire is advanced into the body lumen such that it traverses an obstruction in the body lumen, the guidewire having a bend at a portion of the guidewire that traverses the obstruction, the bend creating a gap between the guidewire and the obstruction, the method further comprising orienting a distal most portion of the distal tip so that the distal most portion of the distal tip traverses the obstruction through the gap as the catheter traverses the obstruction. In an embodiment, the orienting of the distal most portion of the distal tip occurs because the catheter self-orients on the guidewire. In an embodiment, the catheter is a balloon catheter.

The invention provides a method of advancing a catheter into a body lumen of a patient comprising: providing a catheter, the catheter comprising an elongate shaft, a distal tip, and a lumen extending proximally from the distal tip, a distal end of the distal tip being oriented at an angle other than 90 degrees to the lengthwise axis of the catheter tip, the distal tip comprising a tapered region, and the catheter being a balloon catheter; loading a guidewire into the lumen of the catheter; advancing the guidewire into the body lumen; and advancing the catheter over the guidewire into the body lumen. In an embodiment, the catheter traverses an obstruction in the body lumen. In another embodiment, the body lumen is a blood vessel. In an embodiment, the guidewire is advanced into the body lumen such that it traverses an obstruction in the body lumen, the guidewire having a bend at a portion of the guidewire that traverses the obstruction, the bend creating a gap between the guidewire and the obstruction, the method further comprising orienting a distal most portion of the distal tip so that the distal most portion of the distal tip traverses the obstruction through the gap as the catheter traverses the obstruction.

With reference now to the various drawing figures, a description is provided of embodiments that are examples of how inventive aspects in accordance with the principles of the present invention may be practiced. It is to be understood that both the foregoing general description and the following detailed description are exemplary and explanatory only and are not restrictive of the broad inventive aspects disclosed herein. It will also be appreciated that the inventive concepts disclosed herein are not limited to the particular device configurations disclosed herein, but are instead applicable to any number of different device configurations.

FIG. 1 illustrates catheter 10 having hub 12, shaft 14, lumen 16 and tip 18. Hub 12 may be comprised of a luer fitting made of polycarbonate or similar materials, and may be configured for attachment to a syringe (not shown) or extension tube (not shown) for administration of fluids into a patient, aspiration of substances from a patient, or monitoring a condition (e.g., pressure) within a patient. Hub 12 is attached to shaft 14 using methods such as adhesive bonding or insert molding as are known in the art. Shaft 14 may be comprised of materials such as nylon, polybutylene terephthalate-long chain polyether glycols block copolymer such as HYTREL® polymer, polyether block amide such as PEBAX® polymer, polyethylene, polyimide, metal, polyurethane, or other materials and may be reinforced with braid, coils, fillers, or other substances. In one embodiment shaft 14 is a nylon extruded tube comprising stainless steel braided wire. Shafts having a length of 10 cm to 300 cm are contemplated. In one embodiment, shaft 14 has a length of 20 cm. In other embodiments, shaft 14 has a length of 30 cm, 40 cm, 60 cm, 80 cm, 120 cm, 160 cm, 200 cm, or 250 cm. Shaft outside diameters of 2 Fr (0.07 cm) to 10 Fr (0.33 cm) are contemplated. In one embodiment, shaft 14 has an outside diameter of 2.5 Fr (0.085 cm). In other embodiments, shaft 14 has outside diameters of 3 Fr (0.1 cm), 4 Fr (0.13 cm), 5 Fr (0.17 cm), 6 Fr (0.2 cm), 7 Fr (0.23 cm), 8 Fr (0.27 cm), or 9 Fr (0.3 cm). Lumen 16 slidably accommodates a guidewire (including hostwires or other wires). Guidewires having a length of 20 cm to 320 cm are contemplated, and guidewires having diameters of 0.009" (0.023 cm) to 0.063" (0.16 cm) are contemplated. In one embodiment, lumen 16 accommodates a guidewire having a diameter of 0.010" (0.025 cm). In other embodiments, lumen 16 accommodates a guidewire having a diameter of 0.014" (0.036 cm), 0.018" (0.046 cm), 0.021" (0.053 cm), 0.025" (0.064 cm), 0.035" (0.089 cm), 0.038" (0.097 cm), or 0.063" (0.16 cm).

Shaft 14 may also comprise a balloon, stent, cutter, diagnostic sensor (e.g., temperature, pressure, $pO_2$), or other diagnostic or therapeutic portion, generally mounted to the distal region of the shaft. Shaft 14 may comprise one or more additional lumens, a distal region more flexible than a proximal region, radiopaque marker bands, or radiopaque fillers.

Figure 2:
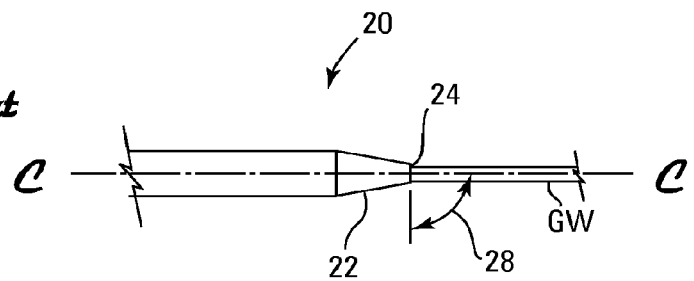
FIG. 2 illustrates a side elevation view of a prior art catheter tip.

Tip 18 is shown in further detail in FIGS. 3A and 3B with guidewire GW shown in phantom line, and in FIG. 4. For comparison purposes a prior art catheter tip is shown in FIG. 2 with guidewire GW shown in phantom line.

Tip 18a in FIG. 3A is comprised of tapered region 32 and end 34. Lumen 16 extends through the tip. Tip lengths of 2 mm to 12 mm are contemplated, and the tip may be comprised of polyether block amide such as PEBAX® polymer, polyurethane, styrene-ethylene-butylene-styrene block copolymer such as C-FLEX® polymer, nylon, or other materials and may be manufactured by insert molding, welding, reflow methods, or other methods as are known in the art. Tip 18a may comprise radiopaque materials to show the orientation of distal most tip 31 under fluoroscopy. For example, longitudinal stripes of radiopaque filler or materials may be incorporated into tip 18a sidewall using extrusion techniques known in the art. Tapered region 32 is formed having angle 37 relative to axis A-A of tip 18. Angles 37 of 1° to 16° are contemplated. In one embodiment, angle 37 is 1.5°. In other embodiments, angle 37 is 2°, 4°, 6°, 8°, 10°, 12°, or 14°. In still other embodiments, region 32 is not tapered. End 34 has distal most tip 31, is oriented at primary angle 38 relative to longitudinal axis A-A of tip 18, and may be so oriented by molding, cutting, laser cutting, or other methods. Distal most tip 31 may be rounded or otherwise softened to prevent causing damage to body passages during use. Angles 38 of 70° to 20° are contemplated. In one embodiment, angle 38 is 65°. In other embodiments, angle 38 is 60°, 55°, 50°, 45°, 40°, 35°, or 30°.

Tip 18b in FIG. 3B is comprised of tapered region 32 and ends 34a, 34b. Lumen 16 extends through tip. Tip lengths of 2 mm to 20 mm are contemplated, and tip may be comprised of polyether block amide such as PEBAX® polymer, polyurethane, styrene-ethylene-butylene-styrene block copolymer such as C-FLEX® polymer, nylon, or other materials and may be manufactured by insert molding, welding, reflow methods, or other methods as are known in the art. Tip 18b may comprise radiopaque materials to show the orientation of distal most tip 31 under fluoroscopy. For example, longitudinal stripes of radiopaque filler or materials may be incorporated into tip 15b sidewall using extrusion techniques known in the art. Tapered region 32 is formed having angle 37 relative to axis A-A of tip 18b. Angles 37 of 1° to 16° are contemplated. In one embodiment, angle 37 is 1.5°. In other embodiments, angle 37 is 2', 4°, 6°, 8°, 10°, 12°, or 14°. In still other embodiments, region 32 is not tapered. End 34a has distal most tip 31 and is oriented at primary angle 38 relative to axis A-A of tip 18. Distal most tip 31 may be rounded or otherwise softened to prevent causing damage to body passages during use. End 34b is oriented at secondary angle 39 relative to axis A-A of tip 18. Secondary angle 39 is less than primary angle 38. Ends 34a, 34b may be so oriented by molding, cuffing, laser cutting, or other methods. Primary angles 38 of 70° to 20° are contemplated. In one embodiment, primary angle 38 is 65°. In other embodiments, primary angle 38 is 60°, 55°, 50°, 45°, 40°, 35°, or 30°. Secondary angles 39 of 60° to 10° are contemplated. In one embodiment, secondary angle 39 is 55°. In other embodiments, secondary angle 39 is 50°, 45°, 40°, 35°, 30°, 25°, or 20°. The ends 34a, 34b together define a unitary distal opening 42 to the lumen 16 through which a guidewire can be backloaded into the lumen. The distal opening 42 extends through both ends 34a, 34b to the lumen 16 such that the distal opening has a first portion defined by end 34a and oriented at the primary angle 38, and a second portion defined by end 34b and oriented at the secondary angle 39.

FIG. 4 shows a plan view of tip 18a. For illustration purposes the tip of FIG. 3A having a primary angle and no secondary angle is shown. It is understood that the tip of FIG. 3B, comprised of both a primary and a secondary angle, will also have a length L of exposed lumen 16. Because end 34 of tip 18a is formed at angle 38 a length L of lumen 16 is exposed to the exterior surface of catheter 10 through sidewall opening 42. In contrast, prior art catheters 20 (FIG. 2) having tip 22 have no such exposed length or sidewall opening because end 24 of tip 22 is formed at angle 28 of approximately 90° relative to axis C-C of catheter 20. A guidewire GW can be more easily backloaded into lumen 16 of catheter 10 through sidewall opening 42 and distal opening of lumen 16 than backloading a guidewire GW into distal opening (only) of the lumen in prior art catheter 20. This is because the combined distal luminal openings in catheter 10 are larger than the distal luminal opening in prior art catheter 20.

Figure 5:
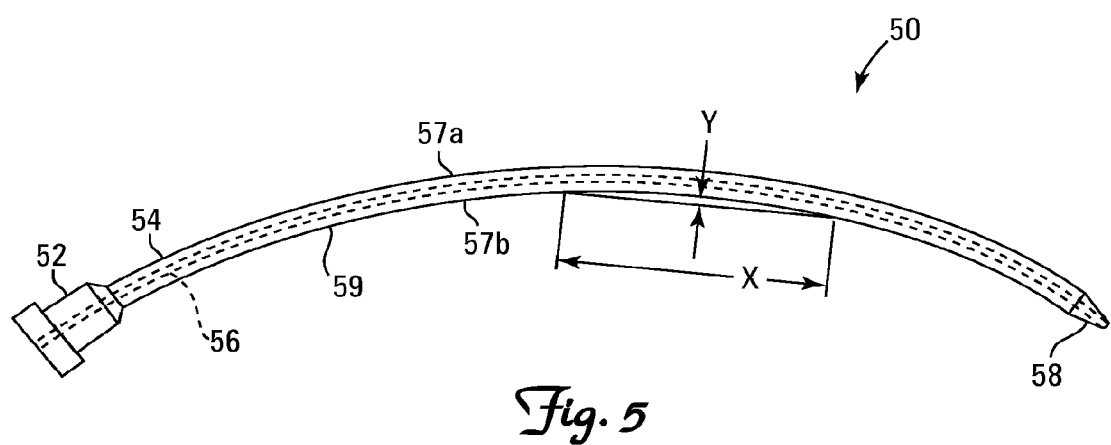
FIG. 5 illustrates a side elevation view of an alternative embodiment of a catheter having features in accordance with the principles of the present disclosure.

FIG. 5 illustrates an alternative embodiment of a catheter having features in accordance with the principles of the present invention. Catheter 50 is comprised of hub 52, shaft 54, lumen 56 and tip 58. Hub 52, shaft 54, lumen 56 and tip 58 have substantially the same function and are comprised of substantially the same materials as hub 12, shaft 14, lumen 16, and tips 18a, 18b described above for catheter 10. Additionally, catheter 50 comprises a bend 59 over some or all of shaft 54 length, thereby causing catheter 50 to have convex aspect 57a and concave aspect 57b. Maximum concavity Y, measured over a length X of 10 cm, in the range of 0.2 cm to 2 cm is contemplated. In one embodiment, maximum concavity Y is 0.4 cm. In other embodiments, maximum concavity Y is 0.6 cm, 0.8 cm, 1.0 cm, 1.2 cm, 1.4 cm, 1.6 cm, or 1.8 cm. Concavity Y causes catheter 50 to self-orient on a guidewire GW in a bend in a body passage such that maximum concavity Y will be aligned with the maximum convex curvature of guidewire GW.

An example of a method of using a catheter that more easily allows backloading of a guidewire into the lumen of the catheter and that has improved ability to cross body passage obstructions in a body of a patient is now described. Using techniques well known in the art, guidewire GW is percutaneously inserted into a patient's blood vessel and advanced to a region of interest in the patient's body. Using imaging techniques such as fluoroscopy an obstructed portion of the vessel is identified and the tip of the guidewire is advanced across the obstruction. With reference to FIG. 4, proximal end of guidewire GW is backloaded into tip 18a, 18b, 58 of catheter 10, 50 by placing proximal end of guidewire through opening 42 onto exposed length L of lumen 16, 56 and then sliding guidewire GW proximally into lumen 16, 56.

Catheter 10, 50 is advanced over guidewire GW to a position proximal to vessel V obstruction OB (FIG. 6A) using imaging techniques such as fluoroscopy. Tip 18a, 18b, 58 is oriented relative to obstruction OB such that distal most portion 31 of the tip is positioned at the inside of the bend (FIG. 6A). In this orientation gap 62 will be present between wire GW and obstruction OB when catheter 10, 50 is being pushed across obstruction. Catheter 10, 50 is then pushed to advance distal most portion 31 across obstruction OB (FIG. 6B). Further pushing of catheter 10, 50 across obstruction will cause ends 34, 34b to traverse obstruction OB (FIG. 6C). It is easier to cause ends 34, 34b to traverse obstruction OB because they are at an angle to the catheter axis, in comparison to prior art (FIG. 2) where end 24 is at approximately 90° relative to axis C-C of the catheter forming a ledge at 24 between guidewire GW and tip 22.

Once catheter 10, 50 has been advanced across obstruction OB the desired diagnostic procedure, monitoring, or treatment can be performed.

In an alternative method guidewire GW is advanced while advancing catheter 10, 50 across obstruction OB, to help assure presence of gap 62.

In another method, tip 18a, 18b, 58 is oriented relative to obstruction OB such that distal most portion 31 of the tip is positioned at the outside of the bend and guidewire GW is retracted. Retraction of guidewire GW causes gap 62 to form at the outside of the bend in vessel V. Catheter 10, 50 is then advanced across obstruction OB to cause tip 18a, 18b, 58 to traverse obstruction.

In yet another method, catheter 10, 50 may be sequentially torqued, advanced, and withdrawn until the catheter tip is able to be advanced across the obstruction. In this way multiple tip orientations relative to the obstruction may be tried. In yet another method, catheter 10, 50 may be torqued as it is advanced across obstruction OB.

In an alternative method suitable for body passages that are not straight, catheter 50 is not torqued to orient the catheter tip relative to the obstruction, rather the catheter is allowed to self orient in the bend.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

What is claimed is:

1. A catheter comprising an elongate shaft, a distal tip having a longitudinal axis, and a lumen extending proximally along the shaft from the distal tip and configured to receive a guidewire, a first distal end of the distal tip being oriented at a first angle other than 90 degrees to the longitudinal axis of the distal tip, a second distal end of the distal tip being oriented at a second angle other than 90 degrees to the longitudinal axis of the distal tip, the second distal end of the distal tip being adjacent to the first distal end of the distal tip, the second distal end of the distal tip being proximal of the first distal end of the distal tip, and the second angle being less than the first angle, wherein the first and second distal ends of the distal tip together define a unitary distal opening to the lumen through which a guidewire can be backloaded into the lumen, wherein the distal opening extends through both the first and second distal ends of the distal tip to the lumen such that the distal opening has a first portion defined by the first distal end and oriented at the first angle, and a second portion defined by the second distal end and oriented at the second angle.

2. The catheter of claim 1, wherein the catheter is a balloon catheter.

3. The catheter of claim 1, wherein the lumen extends proximally from the distal end of the distal tip to a proximal end of the shaft.

4. The catheter of claim 1, wherein the distal tip has a length of 2 mm to 12 mm.

5. The catheter of claim 1, wherein the distal tip comprises a tapered region.

6. The catheter of claim 5, wherein the tapered region has an angle relative to the lengthwise axis of the catheter tip of 1 to 16 degrees.

7. The catheter of claim 1, wherein the shaft has a length of 10 cm to 300 cm.

8. The catheter of claim 1, wherein the shaft has a length of 20 cm.

9. The catheter of claim 1, wherein the first angle is 65 degrees.

10. The catheter of claim 1, wherein the first angle is selected from the group consisting of 65, 60, 55, 50, 45, 40, 35, or 30 degrees.

11. The catheter of claim 10, wherein the second angle is selected from the group consisting of 55, 50, 45, 40, 35, 30, 25, or 20 degrees.

12. The catheter of claim 1, wherein the first angle is from 70 degrees to 20 degrees.

13. The catheter of claim 12, wherein the second angle is from 60 to 10 degrees.

14. The catheter of claim 13, wherein the second angle is 55 degrees.

15. The catheter of claim 1, wherein the second angle is 5 to 20 degrees less than the first angle.

16. The catheter of claim 1, wherein the second angle is 10 degrees less than the first angle.

17. The catheter of claim 1, wherein the shaft has a length and the shaft has a bend over at least some of its length.

18. The catheter of claim 17, wherein the shaft has a bend over all of its length.

19. The catheter of claim 17, wherein the shaft has a bend at least from the distal tip to a midpoint of the shaft.

20. The catheter of claim 17, wherein the shaft has a bend at least from the distal tip to a point 25 percent of the shaft length proximal from the distal tip.

21. The catheter of claim 17, wherein the shaft has a bend at least from the distal tip to a point 10 percent of the shaft length proximal from the distal tip.

22. The catheter of claim 17, wherein the shaft has a maximum concavity of from 0.2 cm to 2 cm as measured over a length of 10 cm.

23. The catheter of claim 22, wherein the shaft has a maximum concavity selected from the group consisting of 0.4 cm, 0.6 cm, 0.8 cm, 1.0 cm, 1.2 cm, 1.4 cm, 1.6 cm, and 1.8 cm.

24. The catheter of claim 22, wherein the shaft has a maximum concavity of 0.4 cm.

25. A method of treating a subject, the method comprising:
providing a catheter, the catheter comprising an elongate shaft, a distal tip having a longitudinal axis, and a lumen extending proximally along the shaft from the distal tip and configured to receive a guidewire, a first distal end of the distal tip being oriented at a first angle other than 90 degrees to the longitudinal axis of the distal tip, a second distal end of the distal tip being oriented at a second angle other than 90 degrees to the longitudinal axis of the distal tip, the second distal end of the distal tip being adjacent to the first distal end of the distal tip, the second distal end of the distal tip being proximal of the first distal end of the distal tip, and the second angle being less than the first angle, wherein the first and second distal ends of the distal tip together define a unitary distal opening to the lumen through which a guidewire can be backloaded into the lumen, wherein the distal opening extends through both the first and second distal ends of the distal tip to the lumen such that the distal opening has a first portion defined by the first distal end and oriented at the first angle, and a second portion defined by the second distal end and oriented at the second angle;

advancing a guidewire into a body lumen of a subject;
backloading the guidewire through the unitary distal opening and into the lumen of the catheter; and
advancing the catheter over the guidewire into the body lumen.

26. The method of claim 25, wherein the catheter is a balloon catheter comprising an inflatable balloon adjacent the distal tip.

27. The method of claim 25, wherein said advancing a guidewire comprises traversing an obstruction in the body lumen.

28. The method of claim 25, wherein the body lumen is a blood vessel.

29. The method of claim 25, wherein the shaft has a length, the shaft has a bend over at least some of its length, and the shaft has a maximum concavity of 0.2 cm to 2 cm as measured over a length of 10 cm, and wherein the catheter self-orients on the guidewire such that the maximum concavity is aligned with a maximum convex curvature of the guidewire.

30. The method of claim 25, wherein said advancing a guidewire comprises traversing an obstruction in the body lumen, the guidewire having a bend at a portion of the guidewire that traverses the obstruction, the bend creating a gap between the guidewire and the obstruction, the method further comprising orienting a distal most portion of the distal tip so that the distal most portion of the distal tip traverses the obstruction through the gap as the catheter traverses the obstruction.

31. The method of claim 30, wherein the shaft has a length, the shaft has a bend over at least some of its length, and the shaft has a maximum concavity of 0.2 cm to 2 cm as measured over a length of 10 cm, and wherein the catheter self-orients on the guidewire such that the maximum concavity is aligned with a maximum convex curvature of the guidewire.

* * * * *